US012000833B2

(12) United States Patent
Guillermet-Guibert et al.

(10) Patent No.: US 12,000,833 B2
(45) Date of Patent: Jun. 4, 2024

(54) MARKER FOR PREDICTING THE SENSITIVITY TO PI3K INHIBITORS

(71) Applicants: INSERM (INSTITUT NATIONAL DE LA SANTE ET DE LA RECHERCHE MEDICALE), Paris (FR); UNIVERSITÉ PAUL SABATIER TOULOUSE III, Toulouse (FR); CENTRE NATIONAL DE LA RECHERCHE SCIENTIFIQUE (CNRS), Paris (FR)

(72) Inventors: Julie Guillermet-Guibert, Toulouse (FR); Thibaut Douche, Toulouse (FR); Emmanuelle Mouton-Barbosa, Toulouse (FR); Odile Schiltz, Toulouse (FR); Marie-Pierre Bousquet, Toulouse (FR); Célia Cintas, Toulouse (FR)

(73) Assignees: INSERM (INSTITUT NATIONAL DE LA SANTE ET DE LA RECHERCHE MEDICALE), Paris (FR); UNIVERSITE PAUL SABATIER TOULOUSE III, Toulouse (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 777 days.

(21) Appl. No.: 16/765,345

(22) PCT Filed: Nov. 22, 2018

(86) PCT No.: PCT/EP2018/082245
§ 371 (c)(1),
(2) Date: May 19, 2020

(87) PCT Pub. No.: WO2019/101871
PCT Pub. Date: May 31, 2019

(65) Prior Publication Data
US 2020/0355693 A1 Nov. 12, 2020

(30) Foreign Application Priority Data
Nov. 23, 2017 (EP) ..................................... 17306625

(51) Int. Cl.
*C07K 16/32* (2006.01)
*C07K 16/30* (2006.01)
*G01N 33/574* (2006.01)
*A61K 45/06* (2006.01)
*C07K 7/08* (2006.01)
(52) U.S. Cl.
CPC ..... *G01N 33/57438* (2013.01); *C07K 16/303* (2013.01); *C07K 16/32* (2013.01); *A61K 45/06* (2013.01); *C07K 7/08* (2013.01)
(58) Field of Classification Search
None
See application file for complete search history.

(56) References Cited

FOREIGN PATENT DOCUMENTS

WO 2003/072557 A1 9/2003
WO 2016/089853 A1 6/2016

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Britton et al: "Quantification of Pancreatic Cancer Proteome and Phosphorylome: Indicates Molecular Events Likely Contributing to Cancer and Activity of Drug Targets", PLOS One, vol. 9, No. 3, Mar. 26, 2014.
Denny: "Phosphoinositide 3-kinase α inhibitors: a patent review", Expert Opinion on Therapeutic Patents, vol. 23, No. 7, pp. 789-799, Jul. 1, 2013.
Fong et al: "Myristolyated alanine-rich C kinase substrate (MARCKS) : a multirole signaling protein in cancers", Cancer Metastasis, Kluwer Academic Publishers, vol. 36, No. 4, pp. 737-747, 20147-10-16.
Garrett et al: "Combination of antibody that inhibits ligand-independent HER3 dimerization and a p110[alpha] inhibitor potently blocks PI3K signaling a growth of HER2+ breast cancers.", Cancer Research, vol. 73, No. 19, pp. 6013-6023, Aug. 5, 2013.
Hosford et al: "Combined Inhibition of both p110 alpha and p110 beta Isoforms of Phosphatidylinositol 3-Kinase Is Required for Sustained Therapeutic Effect in PTEN-Deficient, ET+ Breast Cancer", Clinical Cancer Research, vol. 23, No. 11, pp. 2795-2805, Jun. 1, 2017.
Jamieson et al: "A drug targeting only p110[alpha] can block phosphoinositide 3-kinase signalling and tumour growth in certain cell types", Biochemical Journal, Portland Press Ltd, vol. 428, No. 1, pp. 53-62, Aug. 15, 2011.

(Continued)

*Primary Examiner* — Meera Natarajan
(74) *Attorney, Agent, or Firm* — WCF IP

(57) ABSTRACT

PI3K signalling is the most increased pathway in human cancers. The four isoforms of PI3K are thought to be activated by different redundant mechanisms leading to a common downstream signalling. However, the mutational pattern of PI3K pathway or its level of expression is not sufficient to predict the sensitivity to PI3K inhibitors. By identifying for the first time a phosphopeptide that predict the sensitivity to p110α and/or p110γ inhibitors, the inventors provide insight in how to handle heterogeneity of PI3K expression patterns in tumoral samples for the choice of available PI3K-targetting drugs. Accordingly, the present relates to a phosphopeptide characterized by the amino acid sequence as set forth in SEQ ID NO:1 (PGTPSDHQSQEASQFER) wherein the threonine residue at position 3 is phosphorylated.

1 Claim, 7 Drawing Sheets

Figure 1:
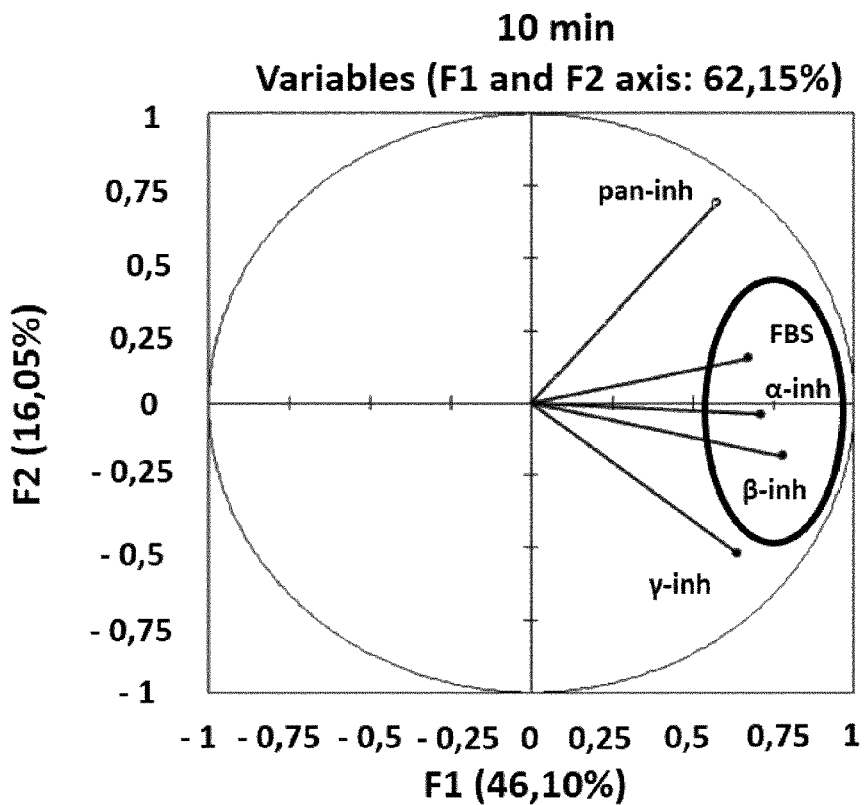
Figure 1:
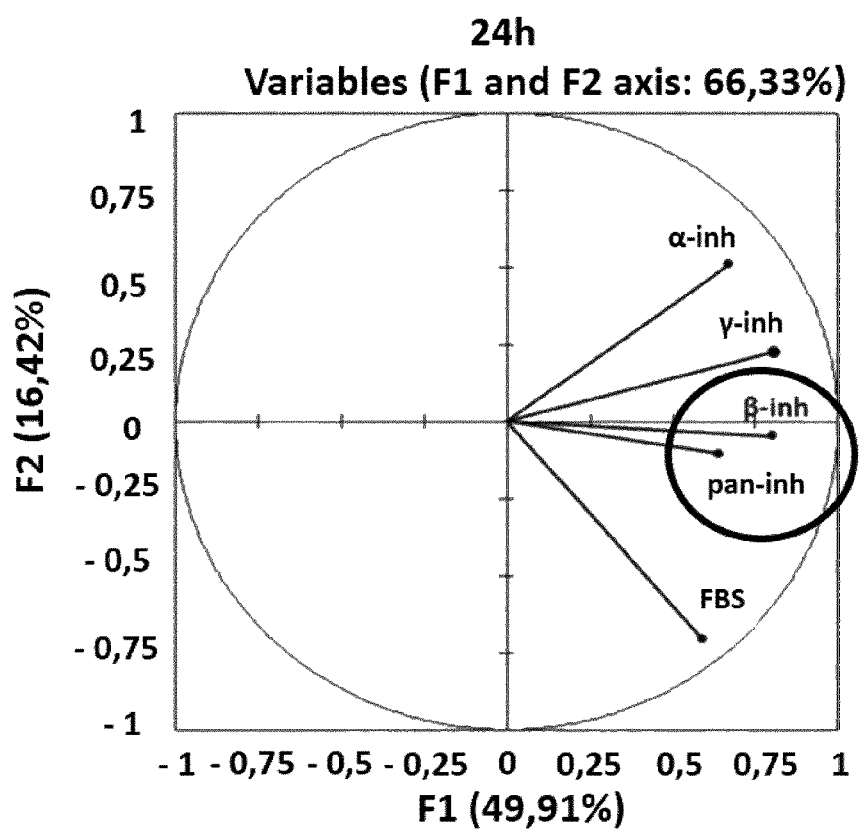
Figure 2A:
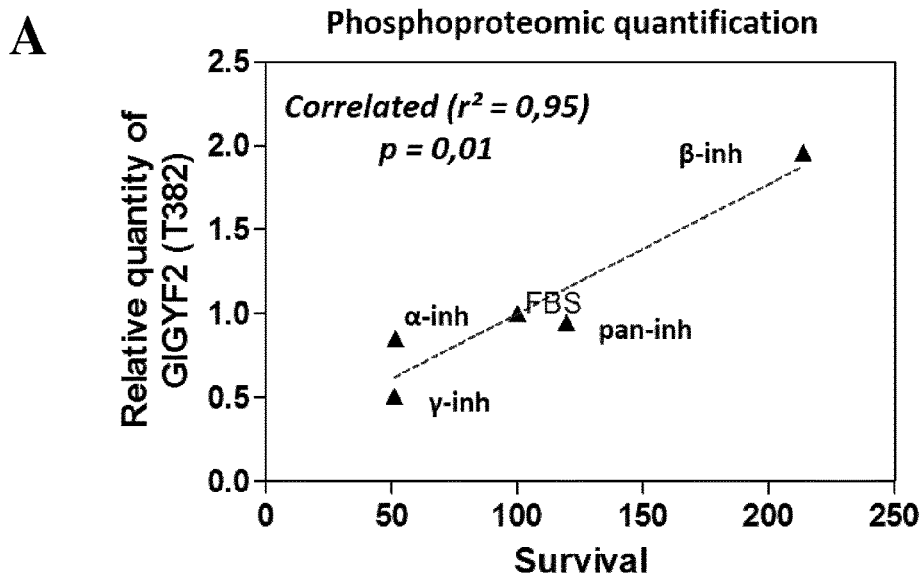
Figure 2B:
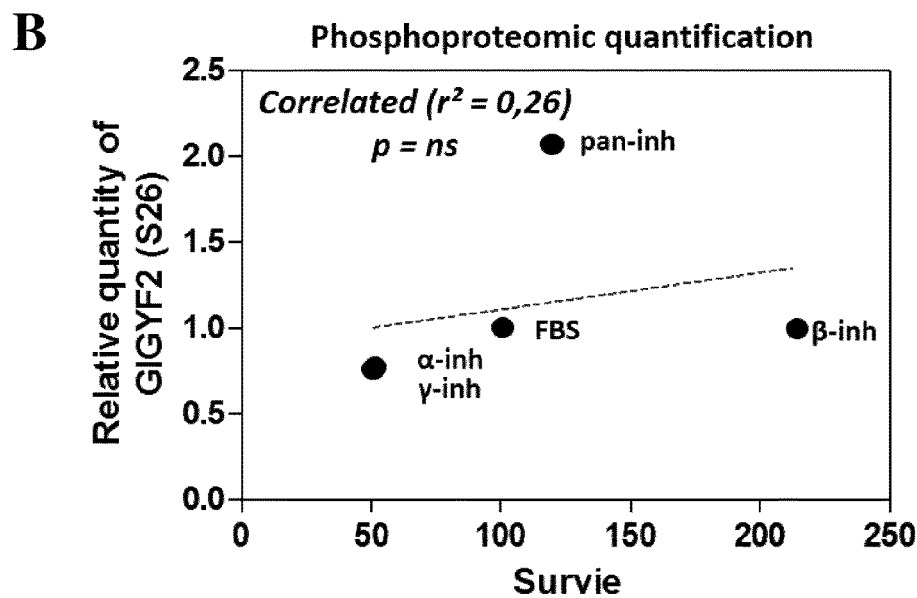
Figure 2C:
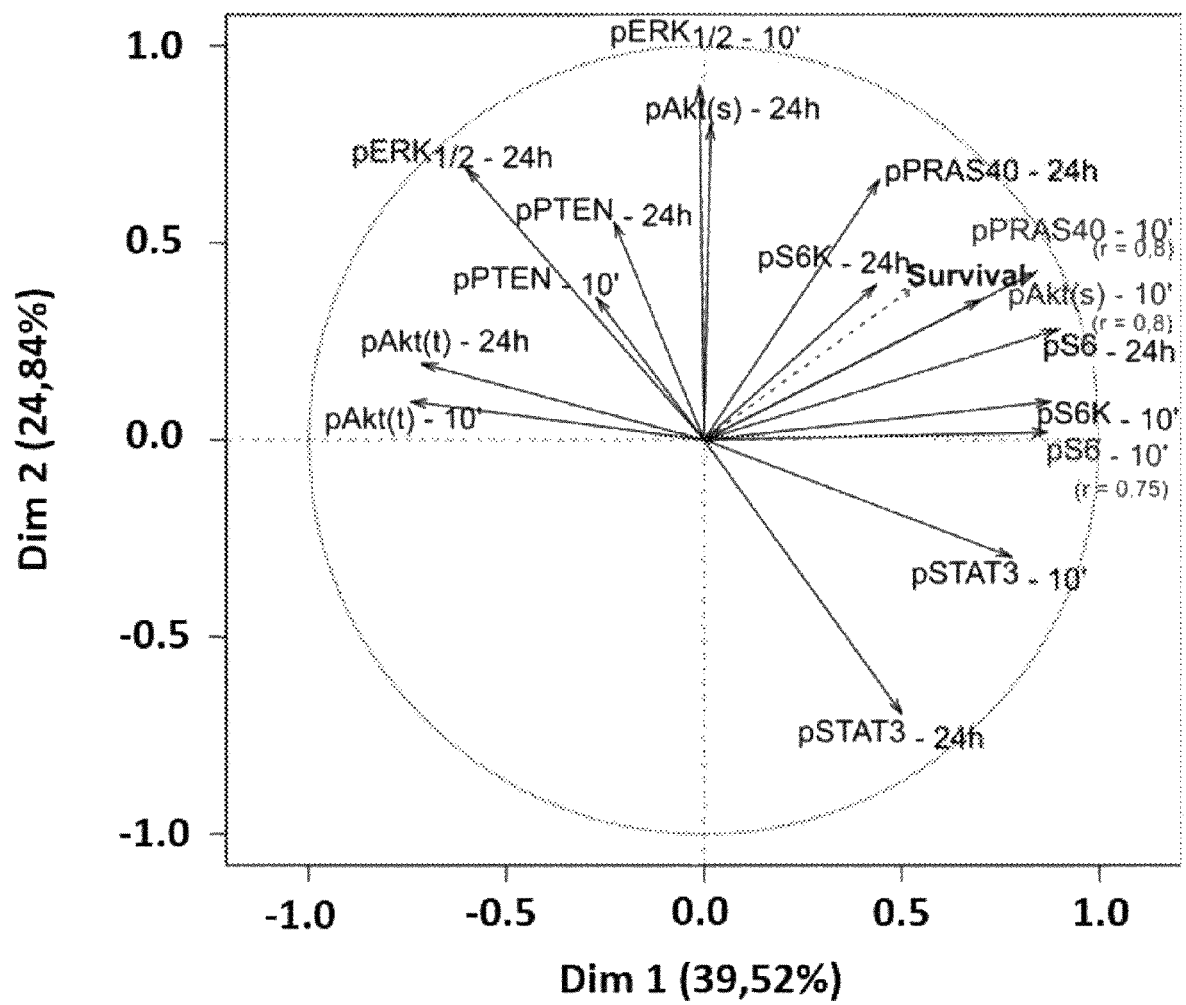
Figure 2D:
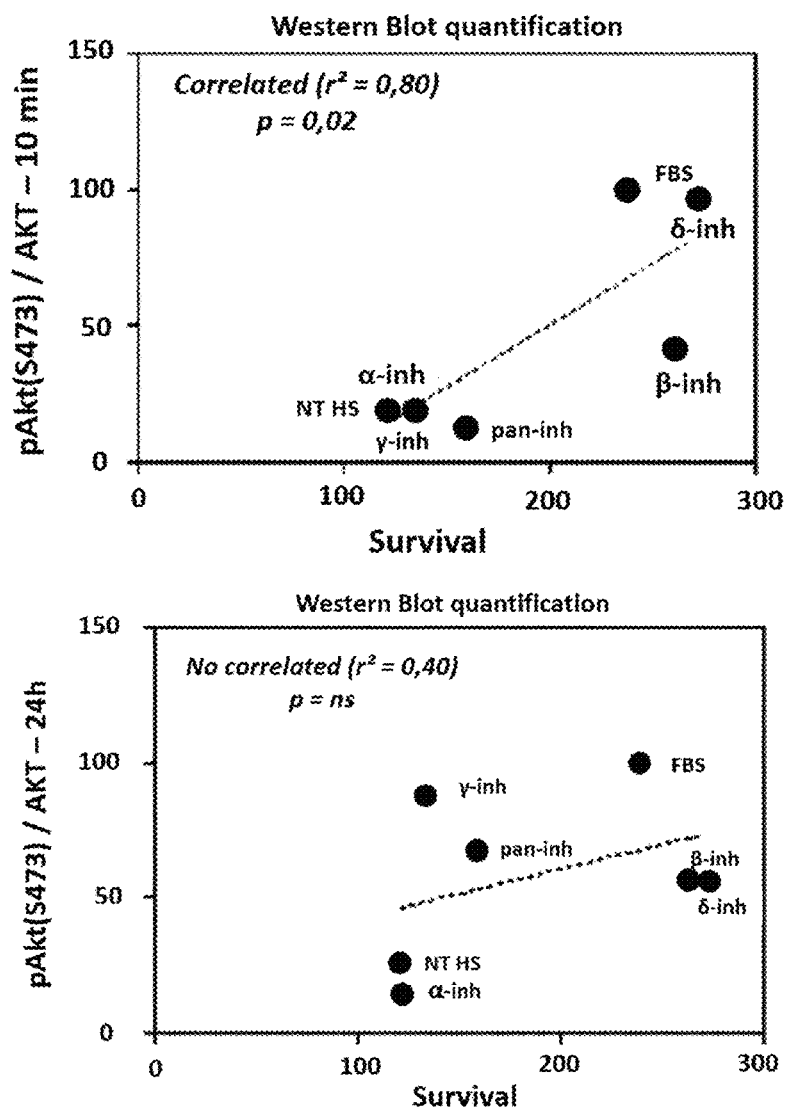

Specification includes a Sequence Listing.

(56) References Cited

OTHER PUBLICATIONS

Mielcke et al: "Activity of novel quinoxaline-derived chalcones onin vitroglioma cell proliferation", European Journal of Mediclinal Chemistry, vol. 48, pp. 255-264, Dec. 22, 2011.
Mielcke et al: "Mechanisms underlying the antiproliferative effects of a series of quinoxaline-derived chalcones", Scientific Reports, vol. 7, Nov. 20, 2017.
Nilsson et al: "Quantitative Phosphoproteomic Analysis of the STAT3/IL-6/HIG1[alhpa] Signaling Network: An Initial Study in GSC11 Glioblastoma Stem Cells", Journal of Proteome Research, vol. 9, No. 1, pp. 430-443, Jan. 4, 2010.
Pons-Tostivint et al: "Targeting PI3K Signaling in Combination Cancer Therapy", Trends in Cancer Jun. 2017, vol. 3, No. 6, pp. 454-469, Jun. 2017.

* cited by examiner

MARKER FOR PREDICTING THE SENSITIVITY TO PI3K INHIBITORS

FIELD OF THE INVENTION

The present invention relates to a new marker for predicting the sensitivity to PI3K inhibitors.

BACKGROUND OF THE INVENTION

Intracellular signalling process is studied in a linear way: stimulation-activation-downstream signalling cascade. Physiopathological signalling does not occur in this way, several stimuli being integrated and regulated at long term. Similarly, inhibition of signalling pathway by molecularly targeted therapies towards signal transduction enzymes also induces an adaptation of the entire signalling network.

Class I PI3Ks are crucial signal transduction enzymes. Across species, the dogma for their involvement in cell signalling is the following: after acute stimulation, PI3K phosphorylates the lipid second messenger phosphatidylinositol 4,5-biphosphate into PI-3,4,5-triphosphate at the plasma membrane, further activating the protein kinases Akt and mTOR, and regulating major cell biology events such as cell proliferation, cell survival and protein synthesis. PI3K is one of the most altered pathways in cancers, and presents 4 different iso forms encoded by 4 different genes [1, 2]. While isoform specificity is well described and accepted in physiology (for review: [1], examples: [3-7]), the use of isoform-selective targeting in cancer is still under debate [8]. The entire signalling axis PI3K/Akt/mTOR is an excellent therapeutic target in cancer, as assessed by the number of molecules currently in clinical trial [8]. However, there is more than Akt/mTOR pathway downstream PI3Ks [9, 10], other signalling routes and feedback loops possibly being integral part of the isoform-specific in vivo role of mammalian PI3Ks. Although cross-regulation between PI3K isoforms upon pharmacological or genetic inhibition is described specific large scale signal transduction and cell adaptation to such treatment is unknown [11-14].

New strategies are needed for the cure of pancreatic cancer patients, due to dramatic lethality rate of this disease. PI3K signalling as assessed by Akt phosphorylation or PI3K/Akt/mTOR gene signature is increased and associated with poor prognosis in patients which underwent surgery [15, 16]. Even if well tolerated, the inhibition of mTOR with RAD001 monotherapy has only a minimal clinical action on gemcitabine-resistant metastatic pancreatic cancer patient (gemcitabine is the standard of line chemotherapy for these pathologies—it improves the well-being of the patient but increases their survival of only a few weeks) [17]. This result is to be correlated with the fact that mTOR inhibitors interfere with a negative feedback loop, which results in an unexpected increase of PI3K signalling and in an increase of the activity of other targets of PI3Ks also regulating proliferation and other protumoral properties. Targeting the upstream PI3k is thus expected to have a better clinical action in these patients. However, prior knowledge of cancer cell adaptation to the inhibition of upstream class I PI3K signalling would be necessary to develop efficient anti-PI3K therapeutic strategy in this disease, where so far all signal-targeted therapies have failed in clinical trials. This knowledge could have an impact to design treatments taking into account these compensation/resistance mechanisms and could explain the specific intrinsic resistance mechanisms of pancreatic cancer cells to signal-targeted therapies. The delimitation of downstream signals and feedback loops is usually restricted to the use of classical phospho-specific antibodies directed against well-known PI3K downstream targets. However, there is still a need for identifying new markers for predicting the sensitivity to PI3K inhibitors.

SUMMARY OF THE INVENTION

The present invention relates to a new marker for predicting the sensitivity to PI3K inhibitors. In particular, the present invention is defined by the claims.

DETAILED DESCRIPTION OF THE INVENTION

PI3K signalling is the most increased pathway in human cancers. The four isoforms of PI3K are thought to be activated by different redundant mechanisms leading to a common downstream signalling. However, the mutational pattern of PI3K pathway or its level of expression is not sufficient to predict the sensitivity to PI3K inhibitors. By identifying for the first time a phosphopeptide that predict the sensitivity p110α and/or p110γ inhibitors, the inventors provide insight in how to handle heterogeneity of PI3K expression patterns in tumoral samples for the choice of available PI3K-targetting drugs.

Accordingly, the first object of the present relates to a phosphopeptide characterized by the amino acid sequence as set forth in SEQ ID NO:1 (PGTPSDHQSQEASQFER) wherein the threonine residue at position 3 is phosphorylated.

As used herein, the term "phosphopeptide" has its general leaning in the art and refers to a phosphorylated peptide on serine, threonine, tyrosine, arginine, lysine or histidine. The term "phosphorylated" in conjunction with peptides is known in the art. As stated above, the term refers to modified forms of peptides, the modified forms being characterized in that one or more phosphate moieties are attached, usually covalently attached, to the peptide.

In some embodiments, the polypeptide of the present invention can be produced by conventional automated peptide synthesis methods. General principles for designing and making phosphopeptides are well known to those of skill in the art.

A further object of the present invention relates to an antibody specific for the phosphopeptide of the present invention.

As used herein, the term "antibody" has its general meaning in the art and refers to any antibody-like molecule that has an antigen binding region, and this term includes antibody fragments that comprise an antigen binding domain such as Fab', Fab, F(ab')2, and single domain antibodies (DABs), In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

As used herein, the term "specificity" refers to the ability of an antibody to detectably bind an epitope presented on the phosphopeptide of the present invention, while having relatively little detectable reactivity with other phosphopeptides. Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules. The term "affinity", as used herein, means the strength of the binding of an antibody to an epitope. The affinity of an antibody is given by the dissociation constant Kd, defined as $[Ab]\times[Ag]/[Ab-Ag]$, where [Ab–Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

In some embodiments, the antibody is a polyclonal antibody or a monoclonal antibody. Monoclonal antibodies may be generated using the method of Kohler and Milstein (Nature, 256:495, 1975). To prepare monoclonal antibodies useful in the invention, a mouse or other appropriate host animal (e.g. mouse, goat, camelid . . . ) is immunized at suitable intervals (e.g., twice-weekly, weekly, twice-monthly or monthly) with the phosphopeptide of the present invention. The animal may be administered a final "boost" of the antigenic form within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, immunofluorescence, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

In some embodiments, one or more labels is attached to the antibody, thereby permitting detection of the phosphopeptide. Exemplary labels include radioactive isotopes, fluorophores, ligands, chemiluminescent agents, enzymes, and combinations thereof. Non-limiting examples of labels that can be conjugated to primary and/or secondary affinity ligands include fluorescent dyes or metals (e.g. fluorescein, rhodamine, phycoerythrin, fluorescamine), chromophoric dyes (e.g. rhodopsin), chemiluminescent compounds (e.g. luminal, imidazole) and bioluminescent proteins (e.g. luciferin, luciferase), haptens (e.g. biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g. horseradish peroxidase, alkaline phosphatase, beta-lactamase), radioisotopes (e.g. $^{3}H$, $^{14}C$, $^{32}P$, $^{35}S$ or $^{125}I$) and particles (e.g. gold). The different types of labels can be conjugated to an affinity ligand using various chemistries, e.g. the amine reaction or the thiol reaction. However, other reactive groups than amines and thiols can be used, e.g. aldehydes, carboxylic acids and glutamine. Various enzymatic staining methods are known in the art for detecting a protein of interest. For example, enzymatic interactions can be visualized using different enzymes such as peroxidase, alkaline phosphatase, or different chromogens such as DAB, AEC or Fast Red. In some embodiments, the label is a quantum dot. For example, Quantum dots (Qdots) are becoming increasingly useful in a growing list of applications including immunohistochemistry, flow cytometry, and plate-based assays, and may therefore be used in conjunction with this invention. Qdot nanocrystals have unique optical properties including an extremely bright signal for sensitivity and quantitation; high photostability for imaging and analysis.

A further object of the present invention relates to a method of predicting the sensitivity of cancer cells to a p110α and/or p110γ inhibitor comprising i) detecting the phosphopeptide of the present invention in said cells and ii) concluding that the cancer cells are sensitive to the p110α and/or p110γ inhibitor when the phosphopeptide is detected.

In some embodiments, the method of the present invention is particularly suitable for predicting the sensitivity of pancreatic cancer cells to p110α and/or p110γ selective inhibitors.

A further object of the present invention relates to a method of determining whether a subject suffering from cancer will achieve a response with a p110α and/or p110γ inhibitor comprising i) detecting the phosphopeptide of the present invention in a tumor tissue sample obtained from the subject and ii) concluding that the subject will achieve a response with a p110α and/or p110γ inhibitor when the phosphopeptide is detected in the tumor tissue sample.

The method is thus particularly suitable for discriminating responder from non-responder. As used herein the term "responder" in the context of the present disclosure refers to a patient that will achieve a response, i.e. a patient where the cancer is eradicated, reduced or improved. According to the invention, the responders have an objective response and therefore the term does not encompass patients having a stabilized cancer such that the disease is not progressing after the therapy. A non-responder or refractory patient includes patients for whom the cancer does not show reduction or improvement after the therapy. According to the invention the term "non-responder" also includes patients having a stabilized cancer. Typically, the characterization of the patient as a responder or non-responder can be performed by reference to a standard or a training set. The standard may be the profile of a patient who is known to be a responder or non-responder or alternatively may be a numerical value. Such predetermined standards may be provided in any suitable form, such as a printed list or diagram, computer software program, or other media. When it is concluded that the patient is a non-responder, the physician could take the decision to stop the therapy to avoid any further adverse sides effects.

In some embodiments, the subject suffers from a pancreatic cancer. As used herein the term "pancreatic cancer" or "pancreas cancer" as used herein relates to cancer which is derived from pancreatic cells. In particular, pancreatic cancer included pancreatic adenocarcinoma (e.g., pancreatic ductal adenocarcinoma) as well as other tumors of the exocrine pancreas (e.g., serous cystadenomas), acinar cell cancers, and intraductal papillary mucinous neoplasms (IPMN).

As used herein, the term "PI3K" has its general meaning in the art and refers to a phosphoinositide 3-kinase. PI3Ks belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate (PIP2) giving rise to phosphatidylinosito-3,4,5-trisphosphate (PIP3). PIP3 functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99).

As used herein, the term "p110α inhibitor" has its general meaning in the art and refers to an inhibitor of the catalytic subunit p110 of PI3Kα.

As used herein, the term "p110γ inhibitor" has its general meaning in the art and refers to an inhibitor of the catalytic subunit p110 of PI3Kγ.

In some embodiments, the inhibitor is a selective inhibitor. As used herein, the term "selective inhibitor" generally refers to a compound that inhibits the activity or expression of the more effectively than at least one other isozyme(s) of the PI3K family. A selective inhibitor compound is therefore more selective than conventional PI3K inhibitors such as wortmannin and LY294002, which are "nonselective PI3K inhibitors. Non-limiting examples of inhibitors include compounds, molecules, chemicals, polypeptides and proteins that inhibit and/or reduce the expression and/or activity of the specific p110 subunit. Additional non-limiting examples of inhibitors include ATP-competitive inhibitors. Further non-limiting examples of inhibitors include ribozymes, antisense oligonucleotides, shRNA molecules and siRNA molecules that specifically inhibit and/or reduce the expression or activity of the specific p110 subunit.

Non-limiting examples of p110α selective inhibitors are disclosed in Schmidt-Kittler et al., Oncotarget (2010) 1(5): 339-348; Wu et al., Med. Chem. Comm. (2012) 3:659-662; Hayakawa et al., Bioorg. Med. Chem. (2007) 15(17): 5837-5844; and PCT Patent Application Nos. WO2013/049581 and WO2012/052745, the contents of which are herein incorporated by reference in their entireties. In particular non-limiting embodiments, the p110α selective inhibitor is derived from imidazopyridine or 2-aminothiazole compounds. Further non-limiting examples include those described in William A Denny (2013) Phosphoinositide 3-kinase α inhibitors: a patent review, Expert Opinion on Therapeutic Patents, 23:7, 789-799. Further non-limiting examples include BYL719, INK-1114, INK-1117, NVP-BYL719, SRX2523, LY294002, PIK-75, PKI-587, A66, CH5132799 and GDC-0032 (taselisib). One inhibitor suitable for the present invention is the compound 5-(2,6-dimorpholin-4-yl-pyrimidin-4-yl)-4-trifluoromethyl-pyridin-2-ylamine that is described in WO2007/084786, which is hereby incorporated by reference in its entirety hereto. Another inhibitor suitable for the present invention is the compound (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) that is described in WO 2010/029082, which is hereby incorporated by reference in its entirety hereto.

Suitable p110γ selective inhibitors have been described in U.S. Patent Publication Nos. 2004/0092561 A1, 2005/004195 A1, 2005/020631 A1, 2005/020630 A1, 2004/248954 A1, 2004/259926 A1, 2004/0138199 A1, 2004/01219996 A1, and 2004/0248953 A1, and International Patent Publication No. WO 04/029055 A1, the entire disclosures of which are hereby incorporated herein by reference. Further examples of inhibitors include 2-amino-N-[1-(4-chloro-7-ethoxy-2-methyl-2H-indazol-6-yl)ethyl] pyrazolo[1,5-a]pyrimidine-3-carboxamide; 2-amino-N-[1-(4-chloro-7-ethoxy-2-ethyl-2H-indazol-6-yl)ethyl]pyrazolo [1,5-a]pyrimidine-3-carboxamide; 2-amino-N-[1-(4-chloro-7-ethoxy-1H-indazol-6-yl)ethyl]pyrazolo[1,5-a]pyrimidine-3-carboxamide; 2-amino-N-[1-(4-chloro-7-ethoxy-1-methyl-1H-indazol-6-yl)ethyl]pyrazolo[1,5-a]pyrimidine-3-carboxamide; 2-amino-N-{1-[4-chloro-7-ethoxy-1-(2-methoxyethyl)-1H-indazol-6-yl]ethyl}pyrazolo[1,5-a] pyrimidine-3-carboxamide; 2-amino-N-(1-(4-chloro-7-ethoxy-1-(2-hydroxyethyl)-1H-indazol-6-yl)ethyl)pyrazolo [1,5-a]pyrimidine-3-carboxamide; 2-amino-N-(1-(4-chloro-1-(cyanomethyl)-7-ethoxy-1H-indazol-6-yl)ethyl)pyrazolo [1,5-a]pyrimidine-3-carboxamide; 2-amino-N-(1-(1-benzyl- 4-chloro-7-ethoxy-1H-indazol-6-yl)ethyl)pyrazolo[1,5-a]pyrimidine-3-carboxamide; 2-amino-N-(1-(4-chloro-7-ethoxy-1-isobutyl-1H-indazol-6-yl)ethyl)pyrazolo[1,5-a]pyrimidine-3-carboxamide; 2-amino-N-(1-(4-chloro-1-cyclobutyl-7-ethoxy-1H-indazol-6-yl)ethyl)pyrazolo[1,5-a]pyrimidine-3-carboxamide; 2-amino-N-(1-(4-chloro-7-ethoxy-1-isopropyl-1H-indazol-6-yl)ethyl)pyrazolo[1,5-a]pyrimidine-3-carboxamide; 2-amino-N-(1-(4-chloro-7-ethoxy-2-(2-methoxyethyl)-2H-indazol-6-yl)ethyl)pyrazolo[1,5-a]pyrimidine-3-carboxamide; 2-amino-N-(1-(4-chloro-7-ethoxy-2-(2-hydroxyethyl)-2H-indazol-6-yl)ethyl)pyrazolo[1,5-a]pyrimidine-3-carboxamide; 2-amino-N-(1-(4-chloro-2-(cyanomethyl)-7-ethoxy-2H-indazol-6-yl)ethyl)pyrazolo[1,5-a]pyrimidine-3-carboxamide; 2-amino-N-(1-(2-benzyl-4-chloro-7-ethoxy-2H-indazol-6-yl)ethyl)pyrazolo[1,5-a]pyrimidine-3-carboxamide; 2-amino-N-(1-(4-chloro-7-ethoxy-2-isobutyl-2H-indazol-6-yl)ethyl)pyrazolo[1,5-a]pyrimidine-3-carboxamide; 2-amino-N-(1-(4-chloro-2-cyclobutyl-7-ethoxy-2H-indazol-6-yl)ethyl)pyrazolo[1,5-a]pyrimidine-3-carboxamide; 2-amino-N-(1-(4-chloro-7-ethoxy-2-isopropyl-2H-indazol-6-yl)ethyl)pyrazolo[1,5-a]pyrimidine-3-carboxamide; 2-amino-N-(1-(2-(2-amino-2-oxoethyl)-4-chloro-7-ethoxy-2H-indazol-6-yl)ethyl)pyrazolo[1,5-a]pyrimidine-3-carboxamide; 2-amino-N-(1-(1-(2-amino-2-oxoethyl)-4-chloro-7-ethoxy-1H-indazol-6-yl)ethyl)pyrazolo[1,5-a]pyrimidine-3-carboxamide; 2-amino-N-(1-(2-(but-2-ynyl)-4-chloro-7-ethoxy-2H-indazol-6-yl)ethyl)pyrazolo[1,5-a]pyrimidine-3-carboxamide; 2-amino-N-(1-(1-(but-2-yn-1-yl)-4-chloro-7-ethoxy-1H-indazol-6-yl)ethyl)pyrazolo[1,5-a]pyrimidine-3-carboxamide; 2-amino-N-(1-(4-chloro-7-phenyl-1H-indazol-6-yl)ethyl)pyrazolo[1,5-a]pyrimidine-3-carboxamide; 2-amino-N-(1-(4-chloro-1-methyl-7-phenyl-1H-indazol-6-yl)ethyl)pyrazolo[1,5-a]pyrimidine-3-carboxamide; 2-amino-N-(1-(4-chloro-2-methyl-7-phenyl-2H-indazol-6-yl)ethyl)pyrazolo[1,5-a]pyrimidine-3-carboxamide; 2-amino-N-(1-(4-chloro-1-((1-methyl-1H-pyrazol-3-yl)methyl)-7-phenyl-1H-indazol-6-yl)ethyl)pyrazolo[1,5-a]pyrimidine-3-carboxamide; 2-amino-N-(1-(4-chloro-2-((1-methyl-1H-pyrazol-3-yl)methyl)-7-phenyl-2H-indazol-6-yl)ethyl)pyrazolo[1,5-a]pyrimidine-3-carboxamide; 2-amino-N-(1-(4-chloro-1-(2-morpholinoethyl)-7-phenyl-1H-indazol-6-yl)ethyl)pyrazolo[1,5-a]pyrimidine-3-carboxamide; 2-amino-N-(1-(4-chloro-2-(2-morpholino-2-oxoethyl)-7-phenyl-2H-indazol-6-yl)ethyl)pyrazolo[1,5-a]pyrimidine-3-carboxamide; 2-amino-N-(1-(2-(2-aminoethyl)-4-chloro-7-phenyl-2H-indazol-6-yl)ethyl)pyrazolo[1,5-a]pyrimidine-3-carboxamide; 2-amino-N-(1-(1-(2-aminoethyl)-4-chloro-7-phenyl-1H-indazol-6-yl)ethyl)pyrazolo[1,5-a]pyrimidine-3-carboxamide; 2-amino-N-(1-(3-bromo-4-chloro-7-phenyl-1H-indazol-6-yl)ethyl)pyrazolo[1,5-a]pyrimidine-3-carboxamide; 2-amino-N-(1-(4-chloro-3-methyl-7-phenyl-1H-indazol-6-yl)ethyl)pyrazolo[1,5-a]pyrimidine-3-carboxamide; 2-amino-N-(1-(3,4-dimethyl-7-phenyl-1H-indazol-6-yl)ethyl)pyrazolo[1,5-a]pyrimidine-3-carboxamide; 2-Amino-N-{1-[8-chloro-5-(3-fluorophenyl)-3-methylimidazo[1,5-a]pyridin-6-yl]ethyl}pyrazolo[1,5-a]pyrimidine-3-carboxamide; 2-Amino-N-(1-(8-chloro-5-phenylimidazo[1,5-a]pyridin-6-yl)ethyl)pyrazolo[1,5-a]pyrimidine-3-carboxamide; 2-Amino-N-[1-(8-chloro-5-phenylimidazo[1,5-a]pyridin-6-yl)ethyl]pyrazolo[1,5-a]pyrimidine-3-carboxamide; 2-Amino-N-{1-[5-(3-fluorophenyl)-3,8-dimethylimidazo[1,5-a]pyridin-6-yl]ethyl}pyrazolo[1,5-a]pyrimidine-3-carboxamide; 2-Amino-N-[1-(8-cyano-5-phenylimidazo[1,5-a]pyridin-6-yl)ethyl]pyrazolo[1,5-a]pyrimidine-3-carboxamide; or a pharmaceutically acceptable salt thereof.

As used herein, the term "tumor tissue sample" means any tissue tumor sample derived from the patient. Said tissue sample is obtained for the purpose of the in vitro evaluation. In some embodiments, the tumor sample may result from the tumor resected from the patient. In some embodiments, the tumor sample may result from a biopsy performed in the primary tumour of the patient or performed in metastatic sample distant from the primary tumor of the patient. The tumor tissue sample can be subjected to a variety of well-known post-collection preparative and storage techniques (e.g., fixation, storage, freezing, etc.) prior to determining the expression level of the gene of interest. Typically the tumor tissue sample is fixed in formalin and embedded in a rigid fixative, such as paraffin (wax) or epoxy, which is placed in a mould and later hardened to produce a block which is readily cut. Thin slices of material can be then prepared using a microtome, placed on a glass slide and submitted e.g. to immunohistochemistry (IHC) (using an IHC automate such as BenchMark® XT or Autostainer Dako, for obtaining stained slides). The tumour tissue sample can be used in microarrays, called as tissue microarrays (TMAs). TMA consist of paraffin blocks in which up to 1000 separate tissue cores are assembled in array fashion to allow multiplex histological analysis. This technology allows rapid visualization of molecular targets in tissue specimens at a time, either at the DNA, RNA or protein level. TMA technology is described in WO2004000992, U.S. Pat. No. 8,068,988, Olli et al 2001 Human Molecular Genetics, Tzankov et al 2005, Elsevier; Kononen et al 1198; Nature Medicine.

The term "detecting" according to the invention relates to determining presence or absence of the phosphopeptide of the present invention. It may furthermore comprise quantification.

Methods for detecting the phosphopeptide of the present invention are well known to skilled artisan and may typically involve the antibody of the present invention. For instance, immunohistochemistry may be used for detecting the phosphopeptide of the present invention in the tumor tissue sample. Immunohistochemistry typically includes the following steps i) fixing the tumor tissue sample with formalin, ii) embedding said tumor tissue sample in paraffin, iii) cutting said tumor tissue sample into sections for staining, iv) incubating said sections with the binding partner specific for the phosphopeptide of interest, v) rinsing said sections, vi) incubating said section with a secondary antibody typically biotinylated and vii) revealing the antigen-antibody complex typically with avidin-biotin-peroxidase complex. Accordingly, the tumor tissue sample is firstly incubated with the binding partners having for the phosphopeptide of interest. After washing, the labeled antibodies that are bound to the phosphopeptide of interest are revealed by the appropriate technique, depending of the kind of label is borne by the labeled antibody, e.g. radioactive, fluorescent or enzyme label. Multiple labelling can be performed simultaneously. Alternatively, the method of the present invention may use a secondary antibody coupled to an amplification system (to intensify staining signal) and enzymatic molecules. Such coupled secondary antibodies are commercially available, e.g. from Dako, EnVision system. Counterstaining may be used, e.g. Hematoxylin & Eosin, DAPI, Hoechst. Other staining methods may be accomplished using any suitable method or system as would be apparent to one of skill in the art, including automated, semi-automated or manual systems.

In some embodiments, the resulting stained specimens are each imaged using a system for viewing the detectable signal and acquiring an image, such as a digital image of the staining. Methods for image acquisition are well known to one of skill in the art. For example, once the sample has been stained, any optical or non-optical imaging device can be used to detect the stain or biomarker label, such as, for example, upright or inverted optical microscopes, scanning confocal microscopes, cameras, scanning or tunneling electron microscopes, canning probe microscopes and imaging infrared detectors. In some examples, the image can be captured digitally. The obtained images can then be used for quantitatively or semi-quantitatively determining the amount of the phosphopeptide in the sample, or the absolute number of cells positive for the maker of interest, or the surface of cells positive for the maker of interest. Various automated sample processing, scanning and analysis systems suitable for use with IHC are available in the art. Such systems can include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.). In particular, detection can be made manually or by image processing techniques involving computer processors and software. Using such software, for example, the images can be configured, calibrated, standardized and/or validated based on factors including, for example, stain quality or stain intensity, using procedures known to one of skill in the art (see e.g., published U.S. Patent Publication No. US20100136549). The image can be quantitatively or semi-quantitatively analyzed and scored based on staining intensity of the sample. Quantitative or semi-quantitative histochemistry refers to method of scanning and scoring samples that have undergone histochemistry, to identify and quantify the presence of the specified biomarker (i.e. phosphopeptide). Quantitative or semi-quantitative methods can employ imaging software to detect staining densities or amount of staining or methods of detecting staining by the human eye, where a trained operator ranks results numerically. For example, images can be quantitatively analyzed using a pixel count algorithms and tissue recognition pattern (e.g. Aperio Spectrum Software, Automated QUantitatative Analysis platform (AQUA® platform), or Tribvn with Ilastic and Calopix software), and other standard methods that measure or quantitate or semi-quantitate the degree of staining; see e.g., U.S. Pat. Nos. 8,023,714; 7,257,268; 7,219,016; 7,646,905; published U.S. Patent Publication No. US20100136549 and 20110111435; Camp et al. (2002) Nature Medicine, 8:1323-1327; Bacus et al. (1997) Analyt Quant Cytol Histol, 19:316-328).

Once the phosphopeptide is detected in the tumor tissue sample, the subject is treated with the p110α inhibitor. Accordingly, a further object of the present invention relates to a method of treating cancer (e.g. pancreatic cancer) in a subject in need thereof comprising i) detecting the phosphopeptide of the present invention in a tumor tissue obtained from the subject and ii) administering to the subject a therapeutically effective amount of a p110α and/or p110γ inhibitor when the phosphopeptide is detected at step i).

In some embodiments, the subject is administered with a therapeutically effective combination of at least one p110α inhibitor and at least one p110γ inhibitor.

As used herein, the term "combination" is intended to refer to all forms of administration that provide a first drug together with a further (second, third . . . ) drug. The drugs may be administered simultaneous, separate or sequential and in any order. Drugs administered in combination have biological activity in the patient to which the drugs are delivered. Within the context of the invention, a combination thus comprises at least two different drugs, and wherein one drug is at least one p110α selective inhibitor and wherein the other drug is at least one p110γ selective inhibitor. In some instance, the combination of the present invention results in the synthetic lethality of the cancer cells.

A "therapeutically effective amount" refers to an amount effective, at dosages and for periods of time necessary, to achieve a desired therapeutic result. A therapeutically effective amount of drug may vary according to factors such as the disease state, age, sex, and weight of the individual, and the ability of drug to elicit a desired response in the individual. A therapeutically effective amount is also one in which any toxic or detrimental effects of the antibody or antibody portion are outweighed by the therapeutically beneficial effects. The efficient dosages and dosage regimens for drug depend on the disease or condition to be treated and may be determined by the persons skilled in the art. A physician having ordinary skill in the art may readily determine and prescribe the effective amount of the pharmaceutical composition required. For example, the physician could start doses of drug employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. A therapeutically effective amount of a therapeutic compound may decrease tumor size, or otherwise ameliorate symptoms in a subject. One of ordinary skill in the art would be able to determine such amounts based on such factors as the patient's size, the severity of the patient's symptoms, and the particular composition or route of administration selected. An exemplary, non-limiting range for a therapeutically effective amount of drug is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. As non-limiting examples, treatment according to the present invention may be provided as a daily dosage of the agent of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Typically, the drugs of the present invention are administered to the patient in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a subject, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of the inhibitor of the invention.

The invention will be further illustrated by the following figures and examples. However, these examples and figures should not be interpreted in any way as limiting the scope of the present invention.

FIGURES

FIG. 1: Phospho-regulated signalling pathways are differently regulated in time by PI3K isoforms. The differential quantitative assessment of Capan-1 phosphoproteome at 10 min and 24 h in each condition was statistically evaluated by a principal component analysis (PCA). For each condition, 3600 heavy/light phosphopeptide ratios were identified and quantified.

FIG. 2: Levels of pGIGYF2 is correlated with sensitivity with PI3K isoform-selective inhibitors. A&B. Correlation between the level of phosphopeptide (assessed by SILAC based LC-MS/MS) at 24 h and cell survival in each condition at day 9 after treatment (final output). Phospho T382-GIGYF2 is a p110γ-specific target at both 10 min and 24 h; phospho S26 is a target of all PI3Ks at 24 h. Pvalue and Pearson correlation coefficient, $r^2$, were determined by GraphPad analysis. C, D. The levels of phosphorylation of member (assessed by WB) of the canonical pathway (pS-Akt, pPRAS40, pS6) are correlated with cell survival only at 10 min.

Figures 3A, 3B:
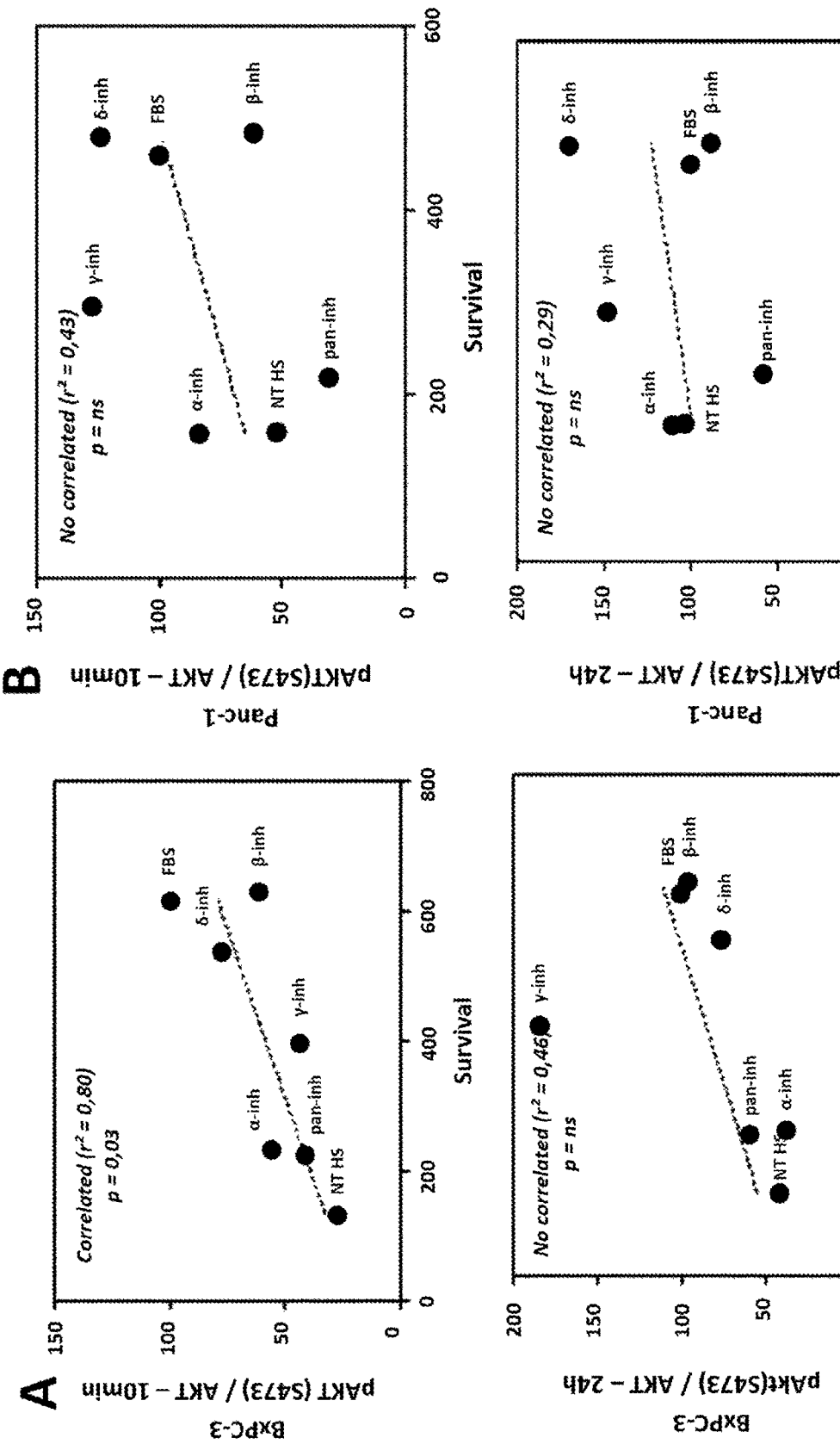
Figure 3C:
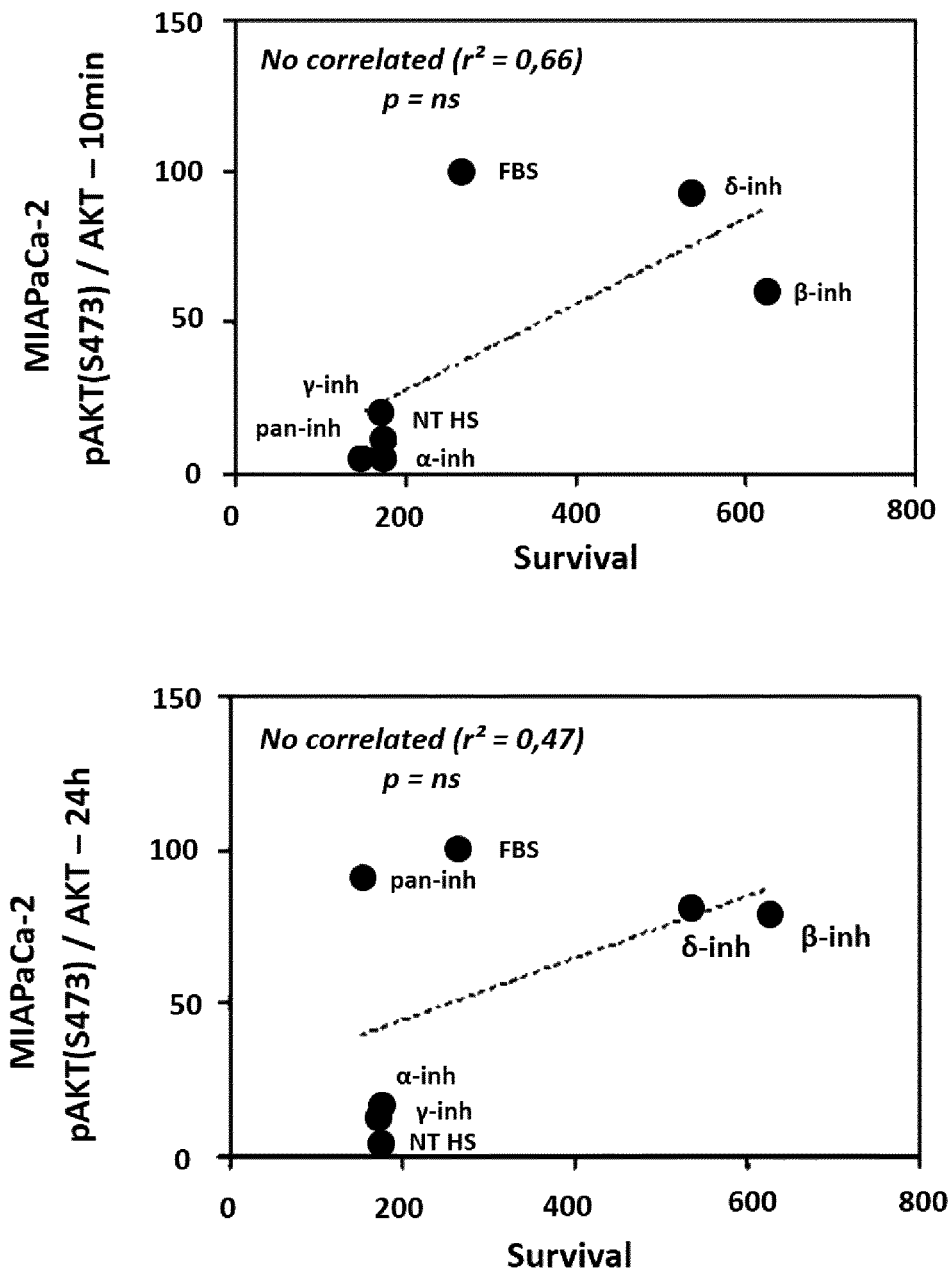

FIG. 3: Levels of pAkt at 24 h is not correlated with sensitivity with PI3K isoform-selective inhibitors. A, B, C. The levels of pSAkt (assessed by WB) are correlated with cell survival at 10 min in BxPC-3.

Figures 4A, 4B:
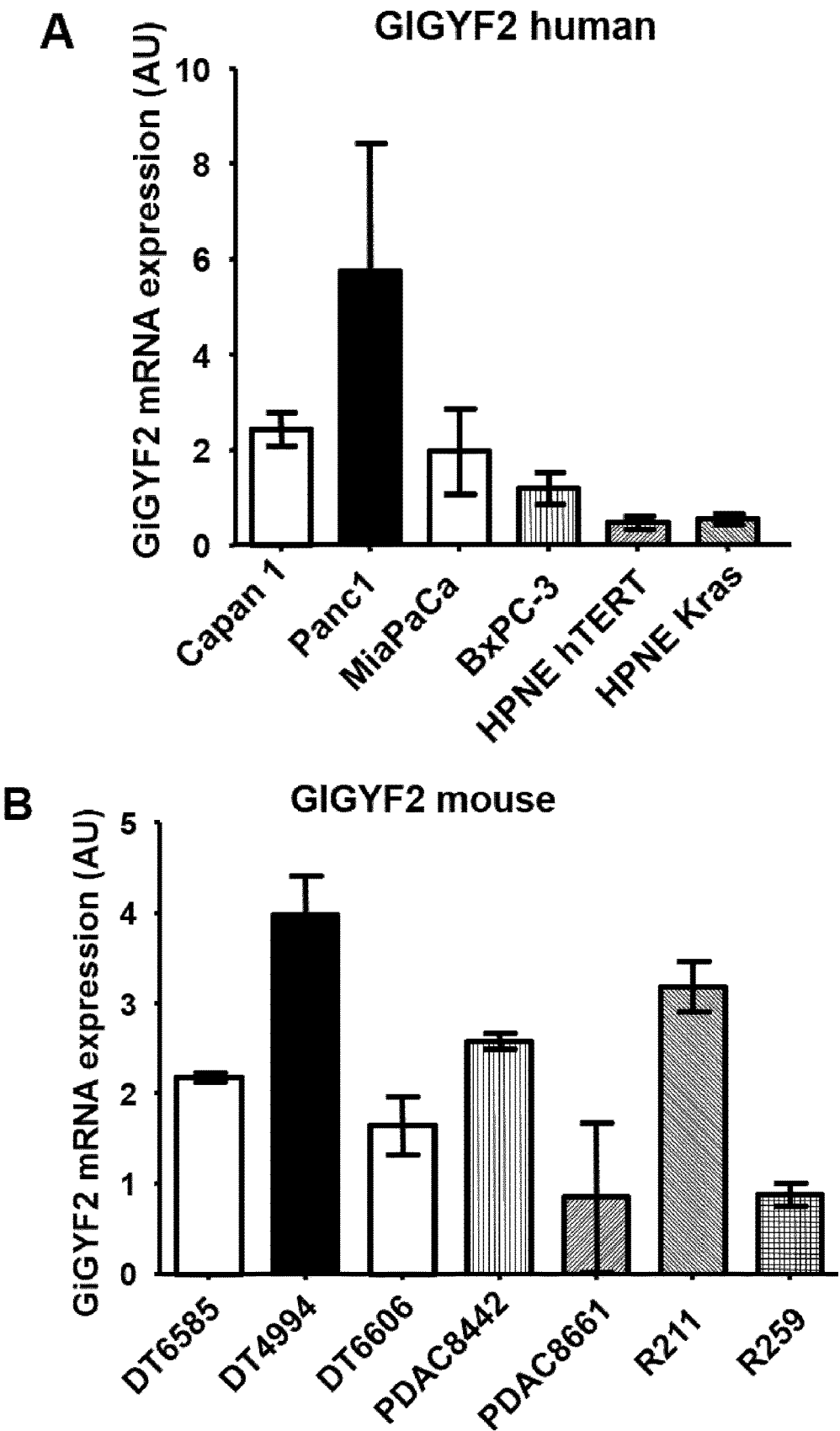

FIG. 4: GIGYF2 mRNA is expressed in human and murine pancreatic cancer cell lines. A Levels of mRNA expression in 4 human pancreatic cancer cell lines as compared to hTERT immortalized HPNE, transformed or not with oncogenic Kras (n=2 or 3). B Expression levels of GIGYF2 in 7 murine pancreatic cancer cell lines derived form in situ murine model of pancreatic cancer.

EXAMPLE

Material & Methods
Cell Lines and Tissue Samples

Human pancreatic ductal cell lines (HPNE, HPNE hTERT and HPDE) were a kind gift from Tsao MS (Toronto, Canada); human pancreatic cell lines (Capan-1, BxPC-3, PANC-1, MIA PaCa-2) came from American Type Culture Collection (ATCC), human acute myeloid leukemia cell line (MOLM4) was a kind gift from Jean-Emmanuel Sarry (CRCT, France) and murine pancreatic cancer cell lines (DT4994, DT6585, DT6606, DT8442, DT8661, R221, R259) were a kind gift from Dieter Saur (Klinikum rechts der Isar der TU München, Germany). Patient organoid cell cultures were obtained by Maximilian Reichert (Klinikum rechts der Isar der TU München, Germany) collected during surgery. Human normal and adenocarcinoma pancreatic samples (>30% tumoral cells) were selected by A Brouchet-Gomez, and collected according French and European legislation (CRB, France). Murine pancreas samples were obtained from LSL-Kras$^{G12D}$; Pdx1-Cre (named KC) and Pdx1-Cre or p110α$^{+/lox}$ (named WT) treated or not with Caerulein to mimic inflammation [39]. Genetic alterations and patient survival curve were performed with TGCA data on cBioPortal web site (cbioportal.org).

In Vitro Culture of Pancreatic Cell Lines

Primary human cells derived from the ducts of the pancreas transduced with an hTERT cDNA, HPNE [40], and transformed with Kras, HPNE Kras [41] were cultured in 25% Medium M3 base (M300F-500, Incell), 75% DMEM without glucose (D5030, Sigma), 2 mM Glutamine (G7513, Sigma), 1.5 g/L sodium bicarbonate (S5761, Sigma), 5% FBS (Gibco), 10 ng/ml EGF (236-EG-200, R&D Systems) and 5.5 mM Glucose (G6152, Sigma). Human Pancreatic duct epithelial cell line HPDE [42] was cultured with Keratinocyte serum-free medium (10724-011, Gibco) supplemented with 0.2 ng/ml EGF and 30 μg Extract pituitary extract bovine (P1476, SIGMA). Human pancreatic cancer cell lines Capan-1 and BxPC-3 were cultured in RMPI 1640 medium. PANC-1, MIA PaCa-2 and all murine pancreatic cancer cells were cultured in Dulbecco's Modified Eagle's Medium with 4.5 g of glucose (D6429, Sigma). All media were supplemented with 10% fetal bovine serum (Eurobio), 1% glutamin (G7513, Sigma) and 1% antibiotics (penicillin/streptomycin, P0781, Sigma). Patient's organoids cell lines were cultured in special medium (Reichert composition, article in preparation). Cells were grown in a humidified incubator at 37° C., 5% CO2. Mycoplasmic free-state was controlled by PCR.

SILAC Labelling of Capan-1 Cell Line

SILAC RPMI medium deficient in L-Lysine and L-Arginine (Fisher Scientific, 1214-2410) was supplemented with 10% dialyzed FBS (Gibco, 26400-044), 1% glutamine (Sigma, G7513-100ML), 1% penicillin/streptomycin (Lonza, 17-605E), and 0.01% plasmocin, and aminoacids: 100 mg/L L-Proline (ULM-8333), 242 mg/L L-Arginine and 40 mg/L L-Lysine. All aminoacids were supplied by Cambridge Isotope Laboratories. For heavy labelling, aminoacids used were the following: L-Arginine-$^{13}C_6$-$^{15}N_4$ hydrochloride (Arg+10 Da) (CNLM-539-H) and L-Lysine-$^{13}C_6$-$^{15}N_2$ dihydrochloride (Lys+8 Da) (CNLM-291-H), whereas in light medium, L-Arginine-$^{12}C_6$-$^{14}N_4$ hydrochloride (ULM-8347) and L-Lysine-$^{12}C_6$-$^{14}N_2$ dihydrochloride (ULM-8766) were added in basal SILAC medium. After 6 passages with respective labelling media (21 days of culture), incorporation of heavy aminoacids was found >95% (as determined by LC-MS/MS). No isotopic arginine/proline conversion was observed. Capan-1 cells cultured in heavy or light SILAC media did show any morphological and proliferation changes compared to cells cultured in standard medium (data not shown).

SILAC Cell Treatment

Light amino acid-labelled and heavy amino acid-labelled Capan-1 cells (respectively called thereafter "light" and "heavy" cells) were washed twice with phosphate buffer saline (PBS; SIGMA; D8537), trypsined (GE Healthcare; L11-002) and plated at a concentration of 2.5.10$^6$ cells in a 14.4 cm-diameter dish (Dutscher, 055063). After 48 h, cells were serum-starved during 16 h, over-night. Light and heavy cells were pre-treated respectively with inhibitors or their accordingly diluted vehicle (DMSO) (for drug description and used concentration) during 1 h, then stimulated or not for 10 min or 24 h with 2% dialysed FBS. After 10 min and 24 h of FBS stimulation, heavy cells and light cells were maintained on ice, washed three times with cold PBS and lysed.

Four biological replicates were sampled for each time point. These biological replicates were performed on four weeks.

SILAC Sample Preparation

Cells were lysed on the plate with 2 mL of lysis buffer (Tris-HCl 100 mM-pH 7.8 (Sigma, T1503), SDS 1% (Sigma, L3771), EDTA 5 mM-pH 7.8 (Euromedex, EU-0007-B), proteases and phosphatases inhibitors (Sigma) containing 1× cOmplete Roche proteases inhibitors cocktail (SIGMA, 04693132001), NaF 10 mM (Sigma, S1504), NaPPi 10 mM (Sigma, S6422) and Na$_3$VO$_4$ 10 mM (Sigma, 450243)) during 30 min at 4° C. in dark. Cells were scraped, harvested and incubated 20 min at 57° C. To eliminate DNA-dependent viscosity, samples were sonicated (amplitude 40%, pulse 1 sec, interval 1 sec during 60 sec). Three other lysis buffers were also tested (Buffer 1: NH$_4$HCO$_3$ 100 mM pH 7.8, Urea 8M; Buffer 2: Tris-HCl 100 mM pH 7.8, Urea 8M; Buffer 3/RIPA: Tris-HCl 50 mM, NaCl 150 mM, Nonidet P-40 1% pH 7.8, SDS 0.1% (w/v)); the chosen buffer allowed the better extraction of phospho-tyrosine proteins as assessed by Western blotting with anti-pY (p-Tyr100) antibody (Cell Signaling Technology; 8954S) (data not shown) as compared to in gel 1-DE profile. Cell lysates were then cleared from insoluble fraction by centrifugation at 10,000×g for 15 min at 25° C., and protein concentration was measured by 2-D Quant kit (GE Healthcare, 80-6483-56). For each biological replicate, light and heavy lysates were mixed at a 1:1 ratio for a total amount of 6 mg.

Protein samples were reduced with 100 mM DTT (Sigma, D9163) for 35 min at 57° C. and then handled according to the FASP (Filter Aided Sample Preparation) digestion protocol [44] using Amicon Ultra-15 Centrifugal Filter device (10 kDa cut-off, MILLIPORE, UFC901096). The 1$^{st}$ step consisted in the replacement of SDS by urea, then a dilution with UA buffer (Tris-HCl 100 mM-pH 8.5, Urea 8M (Sigma, U5128)) and an alkylation with CAA solution (Tris-HCl 100 mM pH 8.5, Urea 8M, Chloroacetamide 50 mM (Sigma, C0267)). For optimization of trypsin efficiency, urea concentration was decreased at 200 mM with Ammonium Bicarbonate buffer (NH$_4$HCO$_3$ 0.05M (SIGMA, 09830) and 10 mM phosphatase inhibitors as previously used in lysis buffer). In a 2$^{nd}$ step, Trypsin (Promega, V5117) digestion was performed at 1:50 (w/w) trypsin:protein ratio overnight at 37° C. on the Amicon Ultra-15 Centrifugal Filter. Tryptic peptides were acidified with 1% trifluoroacetic acid (TFA—Sigma, T6508), cleared at 5,000 rpm for 15 minutes at 15° C., and desalted using C18 Sep-Pak plus cartridges (Waters, WAT043395, 500 mg sorbent). Resin was conditioned with 15 mL in 80% Acetonitrile (ACN—Sigma, 34888) then equilibrated with 15 mL in 0.1% TFA. After the loading step, sample was washed with 15 mL in 0.1% TFA, and the elution was performed with 4 mL in 80% ACN, 0.1% TFA). Eluted peptides were lyophilized with a speed-vacuum overnight.

Protocol for the enrichment with TiO$_2$ beads is based on Larsen et al., [45] and Jensen et al. [46]. In details, dried peptide pellets were resuspended in 1 ml of Titansphere TiO$_2$ blocking buffer (80% ACN, 0.1% TFA, 20 mg/mL Glycolic acid (Sigma, 149357), loaded onto eppendorf tube containing TiO$_2$ using a Tio$_2$ beads/peptides ratio equal to 4, w/w (i.e. 6 mg of peptides for 24 mg of TiO$_2$ beads (GL Sciences Inc, TiO2 NP 100 A 5 µm, 5020-75000)) and incubated 45 min at room temperature under agitation. In advance, the TiO$_2$ beads were washed twice with 2 ml of 0.5% NH$_4$OH (SIGMA, 338818), 40% ACN pH 5 (first washing) and 2 ml of 80% ACN, 0.1% TFA (second washing), and were incubated with blocking buffer. The bound peptides were eluted twice with 400 µl elution buffer (0.5% NH$_4$OH, 4% ACN pH 10.5). To eliminate residual beads, the TiO$_2$ eluates were injected on C8 columns (Dyneon/3M, Empore Cartridge C8-SD 4MM/1ML, 1cc Standard Density, 4114SD), then eluted with 400 µl of 80% ACN, 1% TFA, and were finally splitted in two fractions (10% of the volume was used for TiO2 enrichment fraction—and 90% for phosphotyrosine enrichment, as described hereafter) and were dried with a speed-vacuum. During optimization steps, 20 mg/mL lactic acid (Sigma, 69785), and 20 mg/mL Glycolic acid (Sigma, 124737), and 5 mg/mL DHB were compared for their ability to give the best enrichment of phosphopeptides over total peptides, according to Ayral UK and al., [47]; Glycolic acid was finally chosen as the best blocking agent.

Phospho-Tyrosine enrichment was performed as recommended by the supplier (PTMScan Phospho-Tyrosine Mouse mAb (P-Tyr-100) (Cell Signalling Technology, #5636)). TiO$_2$ enriched dried peptides pellets were resuspended in 350 µl of IAP buffer (50 mM MOPS/NaOH, 10 mM Na$_2$HPO$_4$, 50 mM NaCl pH 7.2-7.4 (Sigma, M9381, 255793, S9888)), sonicated and pH was controlled (neutral pH 6). After four washing of beads with 1×PBS, 5.4 mg of TiO2-enriched peptides were incubated with 18 µl of beads over-night at 4° C. under agitation (Cell Signalling Technology, PTMScan® Phospho-Tyrosine Rabbit mAb (P-Tyr-1000) Kit, #8803S). After 1 min of 2700 g centrifugation, the supernatant (flowthrough, FT) was removed. Phospho-tyrosine peptides were eluted twice with 100 µl of 0.15% Trifluoroacetic acid (TFA, Sigma, T6508), the two eluates were combined and the resulting sample was dried in a speed-Vac.

Data-Dependent Acquisition LC-MS/MS

SILAC samples (TiO$_2$ enriched peptides and flowthrough peptides) were resuspended with 2% acetonitrile, 0.05% TFA and analyzed by nano-LC-MS/MS using an UltiMate 3000 system (Dionex) coupled to LTQ-Orbitrap Velos mass spectrometers (Thermo Fisher Scientific, Bremen, Germany). Five microliters of each peptide sample were loaded on a C18 precolumn (300 µm inner diameter×5 mm; Dionex) at 20 µl/min in 5% acetonitrile, 0.05% trifluoroacetic acid. After 5 min of desalting, the precolumn was switched online with the analytical C18 column (75 µm inner diameter×50 cm; in-house packed) equilibrated in 95% solvent A (5% acetonitrile, 0.2% formic acid) and 5% solvent B (80% acetonitrile, 0.2% formic acid). Peptides were eluted using a 5-50% gradient of solvent B during 310 min at a 300 nl/min flow rate. The LTQ-Orbitrap was operated in data-dependent acquisition mode with the Xcalibur software. Survey scan MS spectra were acquired in the Orbitrap on the 350-1,800 m/z range with the resolution set to a value of 60,000. The twenty (LTQ-Orbitrap Velos) most intense ions per survey scan were selected for CID fragmentation, and the resulting fragments were analyzed in the linear trap (LTQ). Dynamic exclusion was used within 60 s to prevent repetitive selection of the same peptide.

For peptide identification, raw data files were processed in Proteome Discover 1.4.1.14 (Thermo Scientific) and searched against SwissProt human fasta database of Mascot (2014-06, sprot_20140428.fasta, 542782 sequences, high and medium confidence, Q-value=0.5-0.1). Searches were performed with a precursor mass tolerance set to 5 ppm, fragment mass tolerance set to 0.6 Da and a maximum number of missed cleavages set to 2. Static modifications was limited to carbamidomethylation of cysteine, oxidation of methionine, acetylation of N-term protein, phosphorylations of serine, threonine and tyrosine residues, isotopomeric labelled lysine (+8.014199 Da) and isotopomeric labeled arginine (+10.008269 Da +8.014199 Da). Peptides were further filtered using Mascot significance threshold S/N=1.5 and a FDR <0.01 based on q-Value (Percolator). Phospho-site localization probabilities were calculated with phosphoRS 3.1 (maximum PTMs per peptide 10, maximum position isoforms 200).

Phosphoproteomic Data Analysis

Phosphopeptides filtered with Proteome Discoverer 1.4.1.14 (see criteria above) were isolated from peptides.

Median of all median of heavy area was calculated to determine a normalising factor between each biological replicates at the two time of treatment (correction factor=median divided by median of all median). Indeed median of heavy samples (starved untreated cells) across all time and biological replicates is not statistically changed and only 209 phosphopeptides (5%) on 4043 were found significantly variant. Light and heavy areas were further converted in normalised areas allowing statistical comparisons across all conditions at once. Phosphopeptides simultaneously identified and quantified in heavy and light conditions (script in C language), were organised in a list of unique common phosphopeptides in all conditions at 10 min and 24 h and were selected for analysis. Ratios of normalised Light area/normalised Heavy area for each replicates and conditions were centred on FBS/NT condition for identification of phosphopeptides which quantity is varying in a given condition as compared to stimulated FBS condition (centred FBS+inhibitor/NT≥1.4 or ≤0.7). Phosphopeptides which quantities were unchanged were identified. Only the ratios which were changed above and below the thresholds were processed for further analysis. Then, values were centred in line to the highest value for each phosphopeptide. Principle component analysis (PCA, XLSTAT module of excel, ascendant hierarchical clustering with Euclidian distance and Ward's method) was applied. A binary matrix allowed us to allocate these classes of ratios as decreased, increased in each condition if its FBS/NT-centred value was ≥1.4 or ≤0.7. Data representations were performed with bioinformatics tools: Venn diagrams (bioinformatics.psb.ugent.be) and PCA (XLSTAT, excel module, version 2017.4, Addinsoft, USA). Biological functions enrichment was collected with AutoCompare ZE software [48] updated in April 2017 with 14637 biological functions from MSigDB version 6.0 (software.broadinstitute.org/gsea/msigdb), 1893 biological functions from Reactome (reactome.org). Comparison of results between all conditions was performed by nwCompare-Julia (Pont F and al., Proteomics, 2010, sites.google.com/site/fredsoftwares/products/nwcompare---julia). Software called "FindPTM" has been developed to localize phosphates or any other post traductionnal modifications (PTM) positions in proteins sequences starting from the PTMs positions in peptides sequences and the proteins accession numbers. FindPTM align peptides sequences on their corresponding proteins sequences and calculates the PTMs positions on the proteins sequences. FindPTM can process an unlimited number of peptides in an unlimited number of files at a rate of more than 3000 peptides/sec on a Core\texttrademark i7 processor. FinPTM is compatible with Uniprot fasta files. FindPTM output is directly compatible with KEA2 software for phosphosites analysis. The software is free software released under the GNU General Public License (gnu.org/licenses) and available at: sites.google.com/site/fredsoftwares/products/findptm. Empirical kinases were determined using Kinase Enrichment Analysis 2 (KEA2) online software (maayanlab.net/KEA2/).

Statistics

Correlation between proliferation/survival effect and phospho-protein/protein expression levels were obtained by a principal component analysis (PCA) and the calculation of a Pearson r correlation factor, respectively with XLSTAT (version 2017.4, Addinsoft, USA) and GraphPad. The median dose effect or half the maximal inhibitory concentration (IC50) values for each cell line at different time points were determined using CompuSyn software [49] based on the quantitative analysis of dose-effect relationships on multiple drugs or enzyme inhibitors by Chou and Talalay [50]. Combinational index (CI) values were calculated to confirm synergy. CI<1 indicates synergistic effects, CI=1 indicates the mean additive effect of the drugs, and CI>1 represents an antagonistic effect. Experimental data provided at least three biological replicates. Statistically significant differences were performed with GraphPad Prism using the T-tests (paired test): *P<0.05, P<0.01, *P<0.001. Non-significant (ns) if P>0.05.

Results

Conditions of Identification of PI3K Isoform-Specific Adaptative Response

In pancreatic cancer, PI3K signalling is associated with a poor prognosis. Analysis of pS473, pT308 Akt in 11 cancer cell enriched pancreatic cancer samples showed a significant increase in all PDAC tissues as compared to normal adjacent pancreas. However, this was not always coupled to a significant increase in the phosphorylation levels of canonical targets, pPRAS40 or pS6K, in all patients (data not shown), emphasizing the importance of other signalling targets downstream PI3Ks. Long-term inhibition of a core signal node is believed to induce an adaptive modification of the entire signal network. We tested if long-term inhibition of each PI3K isoforms induces a differential change in pancreatic cancer cell adaptation. To answer this question, we devise a strategy to globally identify this adaptive response focusing on phospho-site regulated signalling pathways (data not shown). Amongst the 4 isoforms responsible for the production of PIP3 and Akt activation, the isoforms p110α and p110γ, are identified by us and others to be involved in pancreatic cancerogenesis [18, 19]. The human pancreatic cancer cell line Capan-1 is representative of common genetic alterations found in PDAC (where mutation of Kras is found at 95%, mutation of p53 at 50%, amplification of AKT2 at 6%, amplification of PTEN at 4% [20]) (data shown). Serum, which consist of a combination of RTK and GPCR stimuli mimicking physiopathological signalling, induces after 10 min a significant activation of class I PI3Ks as assessed by the phosphorylation of Akt and known downstream effectors PRAS40, S6K, S6 (data not shown). Pan-PI3K-targeting inhibitors that inhibit all PI3K isoform (here, LY-294002) completely abolish pAkt and all downstream signals (data not shown). Isoform-selective drugs targeting either p110α (α-inh, A66) or p110β (β-inh, TGX-221), p110γ (γ-inh, AS-252424) significantly inhibited pS473 and pT308Akt levels after 10 min stimulation. α-inh and γ-inh respectively inhibited RTK-driven (EGF) or GPCR-driven (LPA) short-term phosphorylation of Akt (data not shown). A 10 min-targeting of all PI3K, or p110α, p110β, p110γ alone, but not p110δ lead to a significant decrease of pAkt and pPRAS40 levels demonstrating the activation of these three PI3K isoforms upon serum stimulation. PI3K inhibitors are still efficient to inhibit pAkt when diluted 24 h in cell medium (data not shown). We thus chose these stimulation conditions to identify differential phosphoproteome across time in response to three PI3K iso form-selective drugs after SILAC metabolic labelling and enrichment in trypsine-based phosphopeptides by TiO2 beads allowing a robust S/T/Y phosphorylation quantification of thousands of proteins.

Strategy of the Phosphoproteomic Approach in Pancreatic Cancer

We devised a spike-in SILAC [21], where we compare all the treatments with heavy labelled untreated cells (data not shown). Incorporation of heavy isotopes was verified by LC-MS/MS after 6 passages (data not shown); this heavy isotope labelling did not change the properties of Capan-1 cell lines (data not shown). We chose to run 4 experimental replicates at two time points 10 min, 24 h in 5 conditions (untreated, serum, serum+pan-PI3K targeting drug, serum+p110α-targeting drug, serum+p110β targeting drug, serum+p110γ targeting drug), allowing statistical analysis of our data. We performed a normalization of all heavy and light areas to the median of each sample, and a centring in column in comparison to FBS/NT ratio. Heavy/light phospho-peptides ratio above or below 1.4/0.7 in at least one condition were selected and the list of modified phosphopeptide ratios for each condition in a time point were then subjected to statistical analysis, namely a principal component analysis and an hierarchical ascendant clustering. All conditions combined, 3600 heavy/light phosphopeptide ratios were identified and quantified by each comparison (data not shown). Amongst these, 79% serine-sites (S), 19% threonine-sites (T), 2% tyrosine-sites (Y) (data not shown) were quantified; these percentages were unchanged upon PI3K inhibition (data not shown). 10 min- and 24 h-serum stimulation induced a modification of phosphopeptides ratios in 557 and 619 phosphopeptides (corresponding to 28 and 32.1% of all identified peptides—data not shown).

Identification of One Phosphopeptide Specifically Regulated by p110γ-in Pancreatic Cancer Cells We then analyzed the phosphoproteome evolution upon PI3K isoform selective inhibition. We showed that phospho-regulated signalling pathways are differently regulated in time by PI3K isoforms (FIG. 1). In particular, we identified one phosphopeptide (pGIGYF2) specifically regulated by the p110γ isoform (FIG. 2). We showed that levels said phosphopeptide are correlated with sensitivity with PI3K isoform-selective inhibitors (FIG. 2) while another identified phosphopeptide is not (FIG. 3). Finally, we showed that the said phosphopeptide mRNA is expressed in human and murine pancreatic cancer cell lines (FIG. 4). Thus the identified phosphopeptide represents a predictive marker of sensitivity to PI3K iso form-selective inhibitor in pancreatic cancer.

REFERENCES

Throughout this application, various references describe the state of the art to which this invention pertains. The disclosures of these references are hereby incorporated by reference into the present disclosure.

1. Vanhaesebroeck, B., et al., The emerging mechanisms of isoform-specific PI3K signalling. Nature Reviews Molecular Cell Biology, 2010. 11(5): p. 329-341.
2. Vanhaesebroeck, B., et al., The emerging mechanisms of isoform-specific PI3K signalling. Nat Rev Mol Cell Biol, 2010. 11(5): p. 329-41.
3. Al-Qassab, H., et al., Dominant Role of the p110 beta Isoform of PI3K over p110 alpha in Energy Homeostasis Regulation by POMC and AgRP Neurons. Cell Metabolism, 2009. 10(5): p. 343-354.
4. Gratacap, M.-P., et al., Regulation and roles of PI3K beta, a major actor in platelet signaling and functions, in Advances in Enzyme Regulation, Vol 51, L.W.G.W-.C.E.F. Cocco, Editor. 2011. p. 106-116.
5. Graupera, M., et al., Angiogenesis selectively requires the p110 alpha isoform of PI3K to control endothelial cell migration. Nature, 2008. 453(7195): p. 662-U9.
6. Guillermet-Guibert, J., et al., The p110 beta isoform of phosphoinositide 3-kinase signals downstream of G protein-coupled receptors and is functionally redundant with p110 gamma. Proceedings of the National Academy of Sciences of the United States of America, 2008. 105(24): p. 8292-8297.
7. Martin, V., et al., Deletion of the p110 beta isoform of phosphoinositide 3-kinase in platelets reveals its central role in Akt activation and thrombus formation in vitro and in vivo. Blood, 2010. 115(10): p. 2008-2013.
8. Pons-Tostivint, E., B. Thibault, and J. Guillermet-Guibert, Targeting PI3K Signaling in Combination Cancer Therapy. Trends Cancer, 2017. 3(6): p. 454-469.
9. Vasudevan, K. M., et al., AKT-independent signaling downstream of oncogenic PIK3CA mutations in human cancer. Cancer Cell, 2009. 16(1): p. 21-32.
10. Castellano, E. and J. Downward, RAS Interaction with PI3K: More Than Just Another Effector Pathway. Genes Cancer, 2011. 2(3): p. 261-74.
11. Foukas, L. C., et al., Critical role for the p110alpha phosphoinositide-3-OH kinase in growth and metabolic regulation. Nature, 2006. 441(7091): p. 366-70.
12. Costa, C., et al., Measurement of PIP3 levels reveals an unexpected role for p110beta in early adaptive responses to p110alpha-specific inhibitors in luminal breast cancer. Cancer Cell, 2015. 27(1): p. 97-108.
13. Schwartz, S., et al., Feedback suppression of PI3Kalpha signaling in PTEN-mutated tumors is relieved by selective inhibition of PI3Kbeta. Cancer Cell, 2015. 27(1): p. 109-22.
14. Leroy, C., et al., Activation of IGF1R/p110beta/AKT/mTOR confers resistance to alpha-specific PI3K inhibition. Breast Cancer Res, 2016. 18(1): p. 41.
15. Schlieman, M. G., et al., Incidence, mechanism and prognostic value of activated AKT in pancreas cancer. Br J Cancer, 2003. 89(11): p. 2110-5.
16. Kong, B., et al., A subset of metastatic pancreatic ductal adenocarcinomas depends quantitatively on oncogenic Kras/Mek/Erk-induced hyperactive mTOR signalling. Gut, 2015. 65(4): p. 647-57.
17. Wolpin, B. M., et al., Oral mTOR inhibitor everolimus in patients with gemcitabine-refractory metastatic pancreatic cancer. J Clin Oncol, 2009. 27(2): p. 193-8.
18. Baer, R., et al., Pancreatic cell plasticity and cancer initiation induced by oncogenic Kras is completely dependent on wild-type PI 3-kinase p110alpha. Genes Dev, 2014. 28(23): p. 2621-35.
19. Edling, C. E., et al., Key role of phosphoinositide 3-kinase class IB in pancreatic cancer. Clin Cancer Res, 2010. 16(20): p. 4928-37.
20. Cancer Genome Atlas Research Network. Electronic address, a.a.d.h.e. and N. Cancer Genome Atlas Research, Integrated Genomic Characterization of Pancreatic Ductal Adenocarcinoma. Cancer Cell, 2017. 32(2): p. 185-203 e13.
21. Geiger, T., et al., Use of stable isotope labeling by amino acids in cell culture as a spike-in standard in quantitative proteomics. Nat Protoc, 2011. 6(2): p. 147-57.
22. Ng, S. S., et al., Wortmannin inhibits pkb/akt phosphorylation and promotes gemcitabine antitumor activity in orthotopic human pancreatic cancer xenografts in immunodeficient mice. Clin Cancer Res, 2001. 7(10): p. 3269-75.
23. O'Reilly, K. E., et al., mTOR inhibition induces upstream receptor tyrosine kinase signaling and activates Akt. Cancer Res, 2006. 66(3): p. 1500-8.
24. Carracedo, A., et al., Inhibition of mTORC1 leads to MAPK pathway activation through a PI3K-dependent feedback loop in human cancer. J Clin Invest, 2008. 118(9): p. 3065-74.

25. Vilar, E., J. Perez-Garcia, and J. Tabernero, Pushing the envelope in the mTOR pathway: the second generation of inhibitors. Mol Cancer Ther, 2011. 10(3): p. 395-403.
26. Garrido-Laguna, I., et al., Integrated preclinical and clinical development of mTOR inhibitors in pancreatic cancer. Br J Cancer, 2010. 103(5): p. 649-55.
27. Javle, M. M., et al., Inhibition of the mammalian target of rapamycin (mTOR) in advanced pancreatic cancer: results of two phase II studies. BMC Cancer, 2010. 10: p. 368.
28. Venkannagari, S., et al., Superior efficacy of co-treatment with dual PI3K/mTOR inhibitor NVP-BEZ235 and pan-histone deacetylase inhibitor against human pancreatic cancer. Oncotarget, 2012. 3(11): p. 1416-27.
29. Fruman, D. A. and C. Rommel, PI3K and cancer: lessons, challenges and opportunities. Nat Rev Drug Discov, 2014. 13(2): p. 140-56.
30. Thorpe, L. M., H. Yuzugullu, and J. J. Zhao, PI3K in cancer: divergent roles of isoforms, modes of activation and therapeutic targeting. Nat Rev Cancer, 2015. 15(1): p. 7-24.
31. Eser, S., et al., Selective requirement of PI3K/PDK1 signaling for Kras oncogene-driven pancreatic cell plasticity and cancer. Cancer Cell, 2013. 23(3): p. 406-20.
32. Zhong, H., et al., Synergistic effects of concurrent blockade of PI3K and MEK pathways in pancreatic cancer preclinical models. PLoS One, 2013. 8(10): p. e77243.
33. Pettazzoni, P., et al., Genetic Events That Limit the Efficacy of MEK and RTK Inhibitor Therapies in a Mouse Model of KRAS-Driven Pancreatic Cancer. Cancer Res, 2015. 75(6): p. 1091-101.
34. Alagesan, B., et al., Combined MEK and PI3K inhibition in a mouse model of pancreatic cancer. Clin Cancer Res, 2015. 21(2): p. 396-404.
35. Junttila, M. R., et al., Modeling targeted inhibition of MEK and PI3 kinase in human pancreatic cancer. Mol Cancer Ther, 2015. 14(1): p. 40-7.
36. Soares, H. P., et al., Dual PI3K/mTOR Inhibitors Induce Rapid Overactivation of the MEK/ERK Pathway in Human Pancreatic Cancer Cells through Suppression of mTORC2. Mol Cancer Ther, 2015. 14(4): p. 1014-23.
37. Diersch, S., et al., Efemp1 and p27(Kip1) modulate responsiveness of pancreatic cancer cells towards a dual PI3K/mTOR inhibitor in preclinical models. Oncotarget, 2013. 4(2): p. 277-88.
38. Morran, D. C., et al., Targeting mTOR dependency in pancreatic cancer. Gut, 2014. 63(9): p. 1481-9.
39. Baer, R., et al., Implication of PI3K/Akt pathway in pancreatic cancer: When PI3K isoforms matter? Adv Biol Regul, 2015. 59: p. 19-35.
40. Lee, K. M., et al., Immortalization with telomerase of the Nestin-positive cells of the human pancreas. Biochem Biophys Res Commun, 2003. 301(4): p. 1038-44.
41. Campbell, P. M., et al., Ras-driven transformation of human nestin-positive pancreatic epithelial cells. Methods Enzymol, 2008. 439: p. 451-65.
42. Furukawa, T., et al., Long-term culture and immortalization of epithelial cells from normal adult human pancreatic ducts transfected by the E6E7 gene of human papilloma virus 16. Am J Pathol, 1996. 148(6): p. 1763-70.
43. Livak, K. J. and T. D. Schmittgen, Analysis of relative gene expression data using real-time quantitative PCR and the 2(-Delta Delta C(T)) Method. Methods, 2001. 25(4): p. 402-8.
44. Wisniewski, J. R., et al., Universal sample preparation method for proteome analysis. Nat Methods, 2009. 6(5): p. 359-62.
45. Larsen, M. R., et al., Highly selective enrichment of phosphorylated peptides from peptide mixtures using titanium dioxide microcolumns. Mol Cell Proteomics, 2005. 4(7): p. 873-86.
46. Jensen, S. S. and M. R. Larsen, Evaluation of the impact of some experimental procedures on different phosphopeptide enrichment techniques. Rapid Commun Mass Spectrom, 2007. 21(22): p. 3635-45.
47. Aryal, U. K. and A. R. Ross, Enrichment and analysis of phosphopeptides under different experimental conditions using titanium dioxide affinity chromatography and mass spectrometry. Rapid Commun Mass Spectrom, 2010. 24(2): p. 219-31.
48. Ycart, B., F. Pont, and J. J. Fournie, Curbing false discovery rates in interpretation of genome-wide expression profiles. J Biomed Inform, 2014. 47: p. 58-61.
49. Chou, T. C., Drug combination studies and their synergy quantification using the Chou-Talalay method. Cancer Res, 2010. 70(2): p. 440-6.
50. Chou, T. C. and P. Talalay, Quantitative analysis of dose-effect relationships: the combined effects of multiple drugs or enzyme inhibitors. Adv Enzyme Regul, 1984. 22: p. 27-55.

The invention claimed is:

1. A method of treating pancreatic cancer in a subject in need thereof comprising
   i) detecting a phosphopeptide having the amino acid sequence as set forth in SEQ ID NO:1 (PGTPSDHQSQEASQFER) wherein the threonine residue at position 3 is phosphorylated in a tumor tissue obtained from the subject and
   ii) administering to the subject a therapeutically effective amount of a small molecule p110α and/or small molecule p110γ inhibitor when the phosphopeptide is detected at step i), wherein the step of detecting is performed by SILAC based LC-MS/MS.

* * * * *

SEQUENCE LISTING

<160> NUMBER OF SEQ ID NOS: 2

<210> SEQ ID NO 1
<211> LENGTH: 17
<212> TYPE: PRT
<213> ORGANISM: Artificial
<220> FEATURE:
<223> OTHER INFORMATION: phosphopeptide

<400> SEQUENCE: 1

Pro Gly Thr Pro Ser Asp His Gln Ser Gln Glu Ala Ser Gln Phe Glu
1               5                   10                  15

Arg

```
<210> SEQ ID NO 2
<211> LENGTH: 19
<212> TYPE: PRT
<213> ORGANISM: Artificial
<220> FEATURE:
<223> OTHER INFORMATION: phosphopeptide

<400> SEQUENCE: 2

Ala Leu Ser Ser Gly Gly Ser Ile Thr Ser Pro Pro Leu Ser Pro Ala
1               5                   10                  15

Leu Pro Lys
```